(12) United States Patent
Chen

(10) Patent No.: US 6,686,065 B2
(45) Date of Patent: Feb. 3, 2004

(54) [5]-HELICENE AND DIBENZOFLUORENE MATERIALS FOR USE IN ORGANIC LIGHT EMITTING DEVICES

(75) Inventor: Jian Ping Chen, San Jose, CA (US)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/012,710

(22) Filed: Dec. 12, 2001

(65) Prior Publication Data

US 2003/0143422 A1 Jul. 31, 2003

(51) Int. Cl.$^7$ .................. H05B 33/12; C07C 211/61; C07C 249/08; C07C 271/107; C07C 285/12
(52) U.S. Cl. .................. 428/690; 428/917; 313/504; 564/426; 548/136; 548/143; 548/262.2; 252/301.16
(58) Field of Search .................. 428/690, 917; 313/504; 252/301.16; 564/404, 426; 548/128, 131, 262.2, 136, 143

(56) References Cited

U.S. PATENT DOCUMENTS

| | | | |
|---|---|---|---|
| 4,720,432 A | 1/1988 | VanSlyke et al. | 428/457 |
| 4,767,873 A | 8/1988 | Katz et al. | 556/42 |
| 4,813,772 A | 3/1989 | Kowel et al. | 350/388 |
| 5,066,796 A | 11/1991 | Law | 540/140 |
| 5,151,629 A | 9/1992 | VanSlyke | 313/504 |
| 5,403,520 A | 4/1995 | Ashitaka et al. | 252/582 |
| 5,698,740 A | 12/1997 | Enokida et al. | 564/308 |
| 5,925,472 A | 7/1999 | Hu et al. | 428/690 |
| 5,936,087 A | 8/1999 | Benson et al. | 546/33 |
| 5,958,517 A | 9/1999 | Crowell et al. | 514/212 |
| 5,993,700 A | 11/1999 | Katz et al. | 252/582 |
| 6,013,383 A | 1/2000 | Shi et al. | 428/690 |
| 6,017,470 A | 1/2000 | Katz et al. | 252/582 |
| 6,051,719 A | 4/2000 | Benson et al. | 548/416 |
| 6,132,641 A | 10/2000 | Rietz et al. | 252/301.16 |
| 6,169,163 B1 | 1/2001 | Woo et al. | 528/397 |
| 6,214,514 B1 | 4/2001 | Evans et al. | 430/133 |

FOREIGN PATENT DOCUMENTS

| | | |
|---|---|---|
| EP | 0832 881 | 4/1998 |
| EP | 0842208 | 5/2000 |
| JP | 5-273614 | 10/1993 |
| JP | 7-285924 | 10/1995 |
| JP | 7-304720 | 11/1995 |
| JP | 9-3023 | 1/1997 |
| JP | 9-77767 | 3/1997 |
| JP | 2000-195673 | 7/2000 |
| WO | WO 97/08262 | 3/1997 |
| WO | WO 99/54385 | 10/1999 |
| WO | WO 00/46321 | 8/2000 |
| WO | WO 01/16252 | 3/2001 |

OTHER PUBLICATIONS

Harvey, R. G., et al., "A New General Synthesis of Polycyclic Aromatic Compounds Based on Enamine Chemistry", J. Org. Chem., 1991, vol. 56, pp. 1210–1217 (No Month).

Willmore, N. D. et al., "A Diels–Alder Route to [5]–and [6]–Helicenes", Angewandte Chemie, Aug. 1992, vol. 31, pp. 1093–1095.

Miyaura, N. and Suzuki A., "Palladium–Catalyzed Cross–Coupling Reactions of Organoboron Compounds", Chemical Reviews, Nov. 1995, vol. 95, No. 7, pp. 2457–2483.

Wang, Z. Y., et al., "New Route to the Introduction of Axial and Helical Chiral Units into Poly(arylene ether)s", Macromolecules, 1997, pp. 8091–8093. (No Month).

Nishiyama, M., et al., "Synthesis of N–Arylpiperazines from Aryl Halides and Piperazine Under a Palladium Tri–tert–butylphosphine Catalyst", Tetrahedron Letters, Feb. 1998, vol. 39, pp. 617–620.

Hartwig, J. F., "Transition Metal Catalyzed Synthesis of Arylamines and Aryl Ethers from Aryl Halides and Triflates: Scope and Mechanism", Angewandte Chemie, Aug. 1998, vol. 37, pp. 2047–2067.

Wolfe, J. P., et al., "Rational Development of Practical Catalysts for Aromatic Carbon–Nitrogen Bond Formation", Acc. Chem Res., Dec. 1998, vol. 31, pp. 805–818.

*Primary Examiner*—Marie Yamnitzky
(74) *Attorney, Agent, or Firm*—Fitzpatrick, Cella, Harper & Scinto

(57) ABSTRACT

Organic materials based on [5] helicenes or dibenzofluorenes are shown to have excellent properties for use in electroluminescent devices, including high stability and efficiency and low excimer formation. The materials may advantageously be adapted to have hole transport or electron transport capabilities in addition to emissive properties.

14 Claims, 1 Drawing Sheet

[5]-HELICENE AND DIBENZOFLUORENE MATERIALS FOR USE IN ORGANIC LIGHT EMITTING DEVICES

BACKGROUND OF THE INVENTION

1. Field of the Invention

The present invention is directed to the field of electroluminescent (EL) devices, and in particular to organic materials for organic light emitting devices (OLEDs).

2. Description of the Related Art

OLEDs are typically comprised of at least a layer of organic luminescent material sandwiched between an anode, typically comprised of a transparent conductor, such as indium-tin oxide and a cathode, typically a low work-function metal, such as magnesium, calcium, aluminum, or the alloys thereof, with other metals. When a bias is applied between the electrodes, positive charges (holes) and negative charges (electrons) are respectively injected from the anode and cathode into the luminescent layer. The holes and the electrons form excitons in the organic layer to emit light.

OLEDs having multiple organic layers are also known. A multilayer OLED may comprise one or more organic hole transport layers adjacent the anode, and one or more organic layers adjacent the cathode which function as both an emissive layer and an electron transport layer. In other structures, a hole transport layer, an emissive layer and an electron transport layer are positioned, in that order, between the anode and the cathode.

Organic materials for EL devices are attractive due to their high luminescence efficiency and because of their high brightness and ease of fabrication by solution processing, such as by spin casting and lithographic printing. On the other hand, it is still desired to find materials having pure emission spectra and good stability to produce cost effective OLEDs having lower driving voltages and higher efficiencies.

SUMMARY OF THE INVENTION

It is an object of the invention to provide an organic material based on [5] helicene or dibenzofluorene suitable for EL devices, having good thermal and morphological stability. In preferred embodiments, these materials are provided with hole transport or electron transport capabilities, in addition to emissive characteristics. These materials are expected to have improved charge injection mobility and charge recombination properties and pure emission spectra.

In preferred embodiments, aromatic amines are bonded to the [5] helicene or dibenzofluorene structures to provide hole transport capability to the subject compounds. Alternatively, electron transport moieties can be bonded to the [5] helicene or dibenzofluorene structures to provide electron transport capability to the materials. Electron deficient species, such as (without limitation) oxadiazole, thiadiazole, and triazole units, may be used for this purpose.

The invention may be embodied as an electroluminescent device, comprising a transparent anode, a cathode, and a layer of emissive [5] helicene or dibenzofluorene material between the anode and the cathode. Electroluminescent devices according to the invention may include an optional hole injection layer adjacent the anode or an electron transport layer adjacent the cathode. In another aspect, the invention encompasses an EL device incorporating a [5] helicene compound or a dibenzofluorene compound having both light emissive and hole transport ability, or both light emissive and electron transport ability.

The invention also encompasses a method of making emissive, hole transport organic materials based on [5] helicenes or dibenzofluorenes by aminating a dibromo [5] helicene or dibenzofluorene in the presence of a phosphorous ligand and Pd(0) catalyst in basic conditions. Similarly, emissive electron transport materials based on [5] helicenes or dibenzofluorenes can be synthesized by attaching an electron withdrawing group, also by means of a Pd(0) catalyst.

This brief summary has been provided so that the nature of the invention may be understood quickly. A more complete understanding of the invention can be obtained by reference to the following detailed description of the preferred embodiment thereof in connection with the attached drawings.

DETAILED DESCRIPTION OF THE PREFERRED EMBODIMENTS

Figure 1:
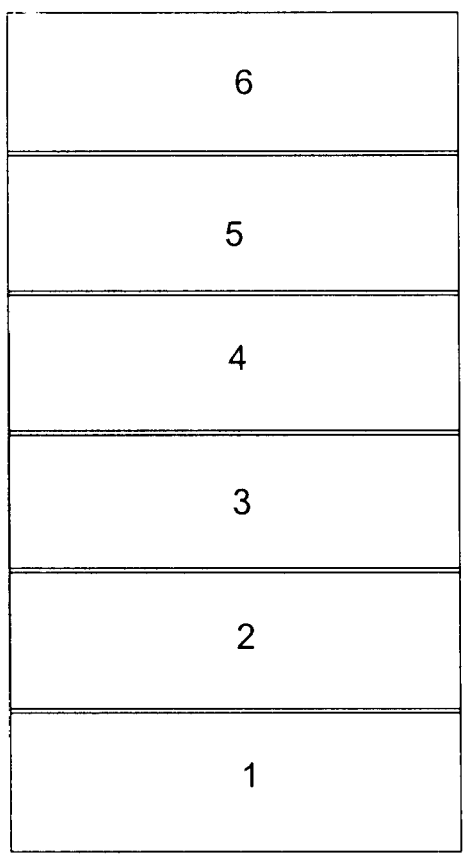
FIG. 1 is a cross-sectional view of an EL device according to the invention.

[5] helicene has the following structure:

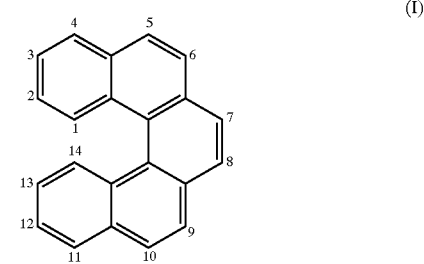

(I)

dibenzofluorene has the following structure:

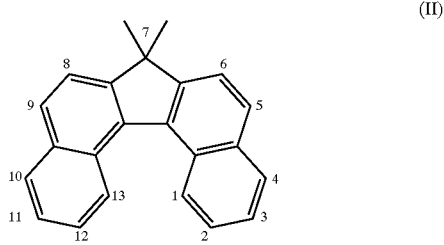

(II)

Both [5] helicene (also called dibenzophenanthrene) and dibenzofluorene comprise five fused rings in ortho arrangement to one another. These five rings form a spiral, non-planar arrangement which prevents close packing.

In addition to the specific substitutions described herein to impart hole transport or electron-transport properties to the subject materials, carbon atoms 1 to 14 in the above Formula (I) and carbon atoms 1 to 13 of Formula (II) can be substituted or unsubstituted, depending upon the starting materials used in their synthesis, or to achieve desired properties in the finished material. Substituents may include, without limitation, halogen atom, alkyl group, substituted alkyl group, alkoxy group, substituted alkoxy group, thioalkoxy group, substituted thioalkoxy group, cyano group, amino group, mono- or disubstituted amino group, hydroxyl group, mercapto group, aryloxy group, substituted aryloxy group, arylthio group, substituted arylthio group, carbocyclic aromatic group, substituted carbocyclic aromatic group, heterocyclic aromatic group, substituted heterocyclic aromatic group, heterocyclic group or a substituted heterocyclic group.

[5] helicene materials suitable for use with the invention, or as starting materials for preparing derivatives according to the invention, can be made using methods known in the art. These include, without limitation, photocyclization of stilbenes, the Diels-Alder reaction of divinylbenzene with a diketone as disclosed in *Angewandte Chemie,* Vol. 31, No. 8, pp. 1093–95 (1992), incorporated herein by reference, and the intramolecular deoxy-olefination of dibenzoylbiaryls as disclosed in *Macromolecules,* Vol. 30, No. 25 pp. 8091–93 (1997), also incorporated herein by reference. Dibromo helicenes and dibromo dibenzofluorenes used as the preferred starting materials in the preparation of the substituted compounds disclosed herein can be prepared by bromination of helicenes and dibenzofluorenes, respectively, by methods well known in the art.

Higher helicenes, having six or more fused benzene rings, are known to have a powerful ability to rotate polarized light. These [6]–[13] helicenes have been proposed for use in non linear optical applications and in EL devices (see U.S. Pat. No. 6,017,470, and JP-A 2000-195673A). [5] helicenes do not exhibit strong optical rotation properties, and have not been heretofore utilized in EL devices.

Dibenzofluorene can be synthesized using methods known in the art, such as those disclosed in R. G. Harvey, et al., "A new general synthesis of polycyclic compounds based on enamine chemistry," *Journal of Organic Chemistry,* Vol. 56, pp. 1210–1217, herein incorporated by reference.

Fluorenes and substituted fluorenes have been proposed for use in EL devices, but not having a non-planar, helical structure like the dibenzofluorenes disclosed herein.

An advantage of the disclosed [5] helicene and dibenzofluorene materials for use in OLEDs according to the invention is that they suppress excimer formation. Excimer formation occurs when pi-orbitals of adjacent emitting molecules interact, with the result that emission peaks at unwanted wavelengths are produced. Without wishing to be bound by theory, it is believed that the non-planar, helical structure of the disclosed materials disrupts pi-bonding between adjacent molecules and suppresses excimer formation.

Another advantage of the disclosed materials for use in OLEDs is their relatively high glass transition temperature ($T_g$). Low $T_g$ materials easily dewet from a deposition surface, leading to difficulties during processing and device instability. The preferred materials according to the invention have $T_g$ greater than about 100° C. and more preferably greater than about 150° C. which permits device fabrication by spin casting, lithography, and the like. It is believed that the steric demand of these helical molecules results in increased solubility, further enhancing their solution processability. In the manufacture of OLEDs, these materials can be processed in neat form with a solvent or in a polymeric matrix.

In particularly preferred embodiments, the above structures (I) and (II) are substituted with arylamine groups, Ar(Ar')NH, to provide the emissive material with hole transport capability, wherein Ar and Ar' are the same or different, substituted or unsubstituted, aromatic groups, such as phenyl, naphthyl, diphenyl, ortho-, meta- or para-terphenyl, or for example, wherein Ar(Ar')NH is carbazole. The aromatic groups Ar and Ar' may themselves be substituted.

Preferred arylamine starting materials include, without limitation:

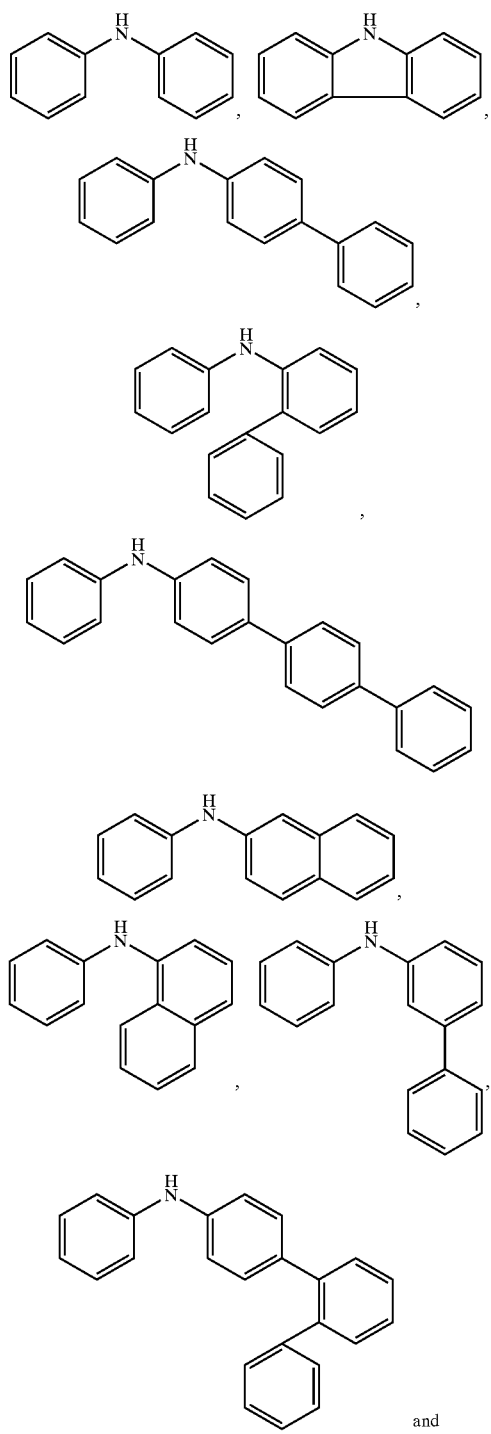

and

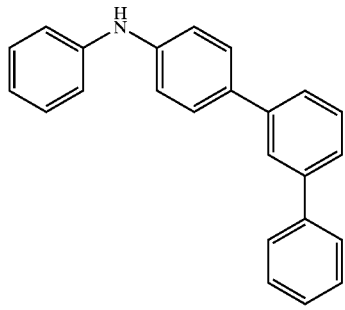

These aromatic amine groups bond through the nitrogen atom to the [5] helicene or dibenzofluorene core. In embodiments wherein arylamine hole-transport moieties are attached to the emissive compounds according to the invention, these groups are preferably substituted at the 7 and 8 positions of the [5] helicene, or at the 5 and 9 positions of the dibenzofluorene.

Electron deficient species may be used to impart electron transport properties to the helical compounds according to the invention, including oxadiazoles, thiadiazoles or triazoles, diaryl sulfones, aryl sulfoxide, fluorinated aryls, biphenyls, diaryl phosphine oxides, and benzophenones. Aryl-substituted oxadiazole, thiadiazole or triazole are particularly preferred.

In preferred embodiments, the invention comprises an EL device having a layer of an organic, emissive, electron transport material having electron withdrawing groups according to one of the following general structures:

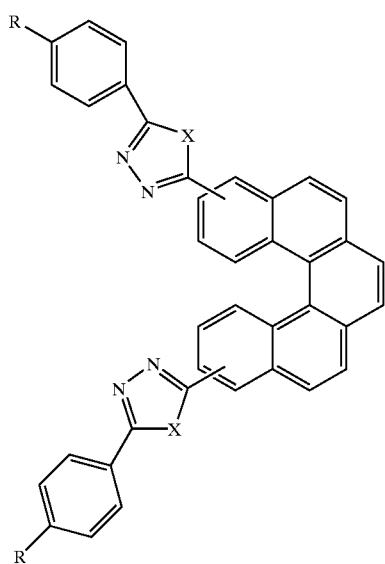

(III)

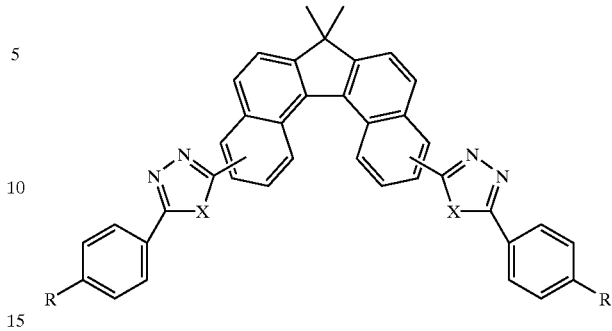

(IV)

wherein X is S, O or N (which nitrogen atom may be substituted) and R is hydrocarbon. In the above structures (III) and (IV), the electron withdrawing moiety can be attached to any of carbons 1–14 of the [5] helicene or any of carbons 1–13 of the dibenzofluorene. In the most preferred embodiments, substitution with electron withdrawing groups is at the 7 and 8 position of the [5]-helicene or at the 5 and 9 position of the difluorobenzene.

Electron withdrawing groups can be incorporated into the target [5] helicene or dibenzofluorene molecules using palladium(0) catalyzed reactions, as described in A. Suzuki, et al. *N. Chem Rev.* 1995 95, 2457, herein incorporated by reference.

Examples 1–4 show the synthesis of [5] helicene materials substituted at the 7 and 8 position with arylamine hole transport groups using a palladium(0) catalyzed amination coupling reaction, starting with a dibromo helicene:

EXAMPLE 1

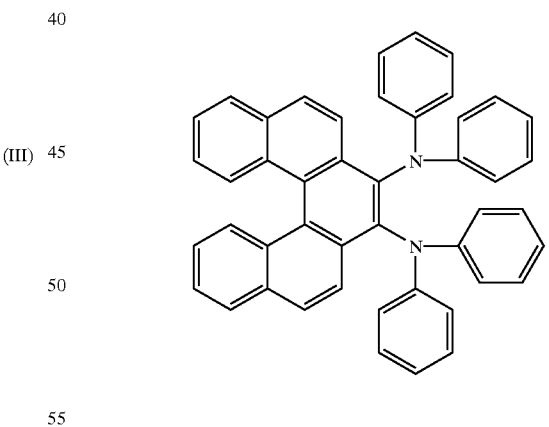

To synthesize 7,8-bis-(N,N'-diphenyl)amino-[5]helicene (structure shown above), a round-flask is charged with 7,8-dibromo[5]helicene (1 mmol), diphenylamine(2 mmol), sodium t-butyloxide (NaOt-Bu) (2.2 mmol), bis(tri-t-butylphosphine)palladium(0) (0.02 mmol) and o-xylene (25 mL). The mixture is stirred at 120° C. under $N_2$ overnight. After cooling down, the mixture is poured into methanol. The precipitate is filtrated, washed with water and methanol, and air-dried. Purification is achieved through silica gel column chromatography.

EXAMPLE 2

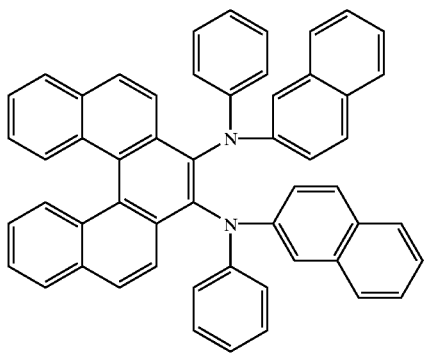

7,8-bis-(N,N'-phenyl-2-naphthyl)amino-[5]helicene (structure shown above) is synthesized in a similar manner as described in Example 1, using N-phenyl-2-naphthylamine in place of diphenylamine.

EXAMPLE 3

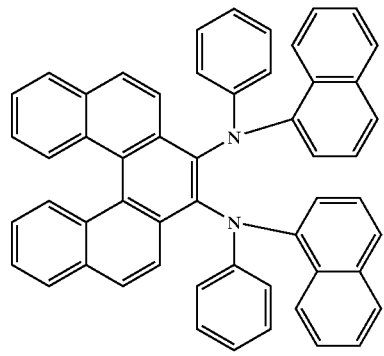

7,8-bis-(N,N'-phenyl-1-naphthyl)amino-[5]helicene (structure shown above) is synthesized in a similar manner as described in Example 1, using N-phenyl-1-naphthylamine in place of diphenylamine.

EXAMPLE 4

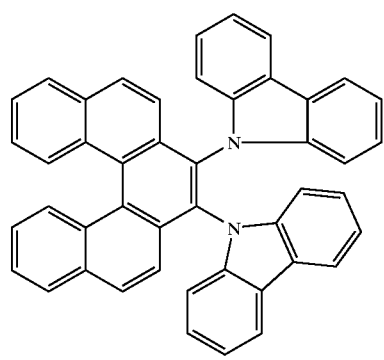

7,8-bis-(N,N'-carbazolyl)-[5]helicene (structure shown above) is synthesized in a similar manner as described in Example 1, using carbazole in place of diphenylamine.

Examples 5–8 show the synthesis of dibenzofluorene materials substituted with arylamine hole-transport groups according to the invention using palladium(0) catalyzed amination coupling reaction.

EXAMPLE 5

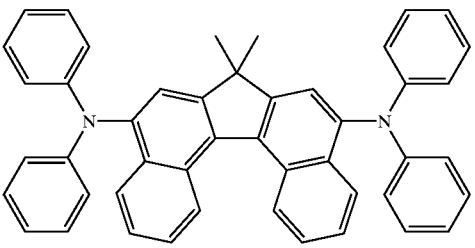

To synthesize 5,9-bis-(N,N'-diphenyl)amino-7,7-dimethyldibenzo[c,g] fluorene (structure shown above), a round-flask is charged with 5,9-dibromo-7,7-dimethyldibenzo[c,g]fluorene (1 mmol), diphenylamine(2 mmol), sodium t-butyloxide (NaOt-Bu) (2.2 mmol), bis(tri-t-butylphosphine)palladium(0) (0.02 mmol) and o-xylene (25 mL). The mixture is stirred at 120° C. under $N_2$ overnight. After cooling down, the mixture is poured into methanol. The precipitate is filtrated, washed with water and methanol, and air-dried. Purification is achieved through silica gel column chromatography using appropriate eluting solvents.

EXAMPLE 6

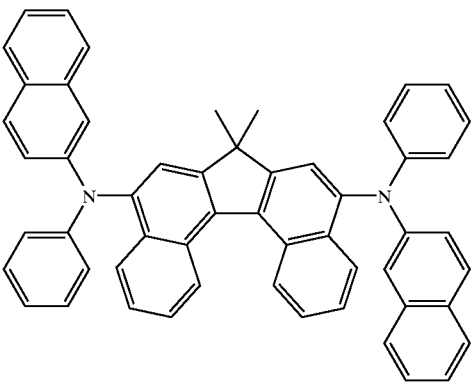

5,9-bis-(N,N'-phenyl-2-naphthyl)amino-7,7-dimethyldibenzo[c,g]fluorene (structure shown above) is synthesized in a similar manner as described in Example 5, using N-phenyl-2-naphthylamine in place of diphenylamine.

EXAMPLE 7

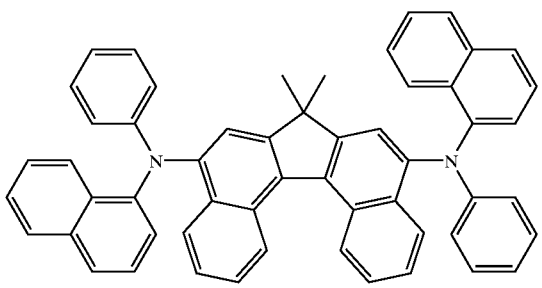

5,9-bis-(N,N'-phenyl-1-naphthyl)amino-7,7-dimethyldibenzo[c,g]fluorene (structure shown above) is synthesized in a similar manner as described in Example 5, using N-phenyl-1-naphthylamine in place of diphenylamine.

EXAMPLE 8

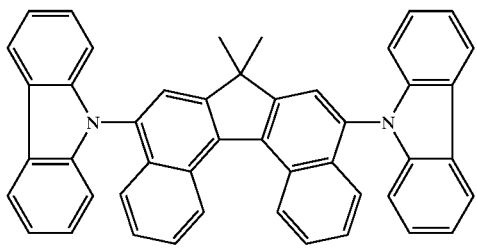

5,9-bis-(N,N'-carbazolyl)-7,7-dimethyldibenzo[c,g] fluorene (structure shown above) is synthesized in a similar manner as described in Example 5 using carbazole in place of diphenylamine.

Example 9 shows the use of a palladium(0) catalyzed Suzuki coupling reaction to prepare an emissive, electron transport material based on [5] helicene.

EXAMPLE 9

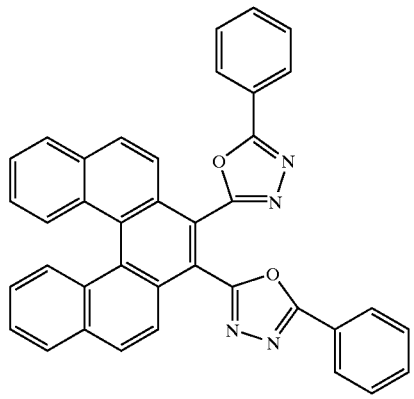

To synthesize 7,8-b is(2'-(5'-phenyl-1',3',4'-oxadiazolyl))-[5] helicene (structure shown above) a round flask is charged with 7,8-dibromo[5]helicene (1 mmol), 2-boronic acid-5-phenyl-1,3,4-oxadiazole (2 mmol), $(PPh_3)_4$ Pd(O) (2 mol %). To this is added a mixture of degassed toluene and aqueous 2M $Na_2CO_3$ (1:1, v/v). The reaction solution is refluxed under nitrogen for 2 days. The whole mixture is then poured into methanol, and the crude product is collected by filtration. The product is purified by silica gel chromatography.

Example 10 shows the use of a palladium(0) catalyzed Suzuki coupling reaction to couple an electron withdrawing group to dibenzofluorene.

EXAMPLE 10

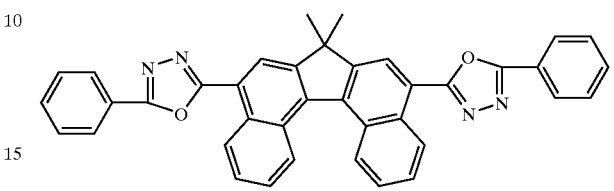

5,9-bis(2'-(5'-phenyl-1',3',4'-oxadiazolyl)-7,7-dimethyldibenzo[c,g] fluorene (structure shown above) is synthesized in a similar manner as described in Example 9, using 5,9-dibromo-7,7-dimethyldibenzo[c,g]fluorene in place of 7,8-dibromo[5]helicene.

FIG. 1 schematically depicts a device according to the invention, including transparent substrate 1, anode 2 adjacent the substrate, optional hole transport layer 3 adjacent the anode, emissive layer 4 based on [5] helicene or dibenzofluorene, optional electron transport layer 5 adjacent the emissive layer, and cathode 6. Each of these layers may itself comprise multiple layers of material having similar composition or function.

Devices according to the invention find use in display applications such as television screens, computer screens and image bar components for digital copiers and printers.

Suitable materials for substrate 1 include glass, quartz and the like, and polymers (including, without limitation, polyesters, polycarbonates, polyacrylates, polymethacrylates, and polysulfones). The thickness of the substrate is not critical and can range, for example, from about 25 to over 1,000 microns, depending on the structural demands of the device.

The anode adjacent the substrate can be comprised of a metal, an alloy, an electroconducting compound, or mixtures thereof, especially with a work function equal to, or greater than about 4 electron volts. Specific examples of anodes include positive charge injecting electrodes such as indium tin oxide (ITO), tin oxide, zinc oxide, gold, platinum, electrically conductive carbon, and conjugated polymers such as polyaniline, polypyrrole, and the like. ITO is preferred. The thickness of the anode can range anywhere from about 10 nanometers to 1 micron.

The hole injecting layer may be comprised of one layer comprising one, two or more hole transport components known in the art. Any conventional known materials which can inject and transport holes into the emissive layer may be employed for forming the hole injecting layer. Preferred hole injecting and hole transporting materials include porphyrin derivatives and aromatic tertiary amines, examples of which are disclosed in U.S. Pat. No. 4,720,432, the disclosure of which is incorporated herein by reference. In embodiments, an emissive/hole transporting layer can be used instead of a hole transport layer. Thus, the hole transport layer 3 is optional.

As an optional electron transport layer any known electron transport materials can be used. AlQ type materials, such as tris-(8-hydroxyquinoline)aluminum and derivatives thereof are particularly preferred. As noted above, electron transport capability can be incorporated into the emissive layer based on [5] helicene or dibenzofluorene materials. Thus, the electron transport layer 5 is optional In embodiments of the present invention, the total thickness of the combined emissive, hole transport and electron transport layers is less than about 1 micron, and preferably is from about 400 angstroms to about 4000 angstroms, sufficient to maintain a current density that permits efficient light emission under a relatively low voltage applied across the electrodes. Suitable thickness of the layers can range preferably from about 50 to about 2,000 angstroms, and preferably from about 400 to 1,000 angstroms.

The cathode 6 can be comprised of any metal, including high or low work function metals. Aluminum, lithium, magnesium and calcium are particularly preferred.

Referring again to the reference numerals of FIG. 1, an OLED according to the invention may be made by first cleaning a glass substrate 1 having an ITO anode 2 patterned thereon in isopropyl alcohol for 5 minutes, followed by rinsing in deionized water for 5 minutes and in isopropyl alcohol again for an additional 5 minutes. The cleaned ITO substrate is placed in a substrate holder of a vacuum deposition chamber and the pressure is reduced to $2 \times 10^{-6}$ Pa. A layer of 4,4',4"-tris(3-methylphenylphenylamino) triphenylamine is deposited as a hole injection layer 3 by vacuum deposition. A layer of [5] helicene material is vacuum-deposited as emissive layer 4. Electron transport layer 5 in a polymeric medium is deposited, followed by an aluminum cathode 6. A driving voltage is applied and a pure color emission is observed.

The foregoing preferred embodiments of substituted [5] helicene and dibenzofluorene materials and the devices made therefrom are for illustration purposes, and are not to be considered limiting of the invention, which is defined by the following claims.

What is claimed is:

1. An electroluminescent device, comprising:
a transparent anode;
a cathode; and
a layer of emissive [5] helicene material between the anode and the cathode,
wherein the [5] helicene material is substituted with two identical arylamino groups of the formula Ar(Ar')N— wherein Ar and Ar' are the same or different, substituted or unsubstituted, aromatic groups, and said [5] helicene material has hole transport ability in said device.

2. The device of claim 1, wherein Ar and Ar' are independently selected from the group consisting of phenyl, naphthyl, diphenyl, ortho-, meta- or para- terphenyl, or wherein Ar(Ar')N— is carbazolyl.

3. The device of claim 1, wherein said [5] helicene material has a glass transition temperature greater than about 100° C.

4. An electroluminescent device, comprising:
a transparent anode;
a cathode; and
a layer of emissive [5] helicene material between the anode and the cathode;
wherein the [5] helicene material is substituted with two identical oxadiazole, thiadiazole or triazole groups, wherein said oxadiazole, thiadiazole or triazole groups may be substituted or unsubstituted, and said [5] helicene material has electron transport ability in said device.

5. An electroluminescent device, comprising:
a transparent anode;
a cathode; and
a layer of emissive dibenzofluorene material between the anode and the cathode having the following structure:

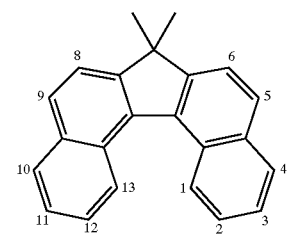

wherein the dibenzofluorene is 5, 9 substituted with two identical arylamino groups of the formula Ar(Ar')N— wherein Ar and Ar' are the same or different, substituted or unsubstituted, aromatic groups, and said dibenzofluorene material has hole transport ability in said device.

6. The device of claim 5, wherein Ar and Ar' are independently selected from the group consisting of phenyl, naphthyl, diphenyl, ortho-, meta- or para- terphenyl, or wherein Ar(Ar')N— is carbazolyl.

7. An electroluminescent device, comprising:
a transparent anode;
a cathode; and
a layer of emissive dibenzofluorene material between the anode and the cathode having the following structure:

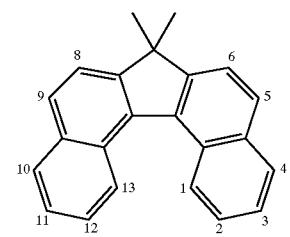

wherein the dibenzofluorene is 5, 9 substituted with an identical diazole or triazole, wherein said diazole or triazole may be substituted or unsubstituted and may contain one or more sulfur or oxygen atoms in the diazole or triazole ring, and said dibenzofluorene material has electron transport ability and emissive ability in said device.

8. A light emissive compound having hole transport capability, and having the following structure (I) or (II):

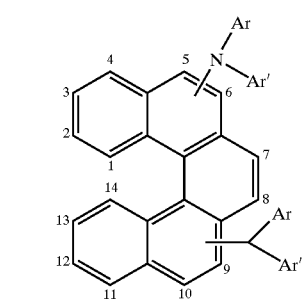
(I)

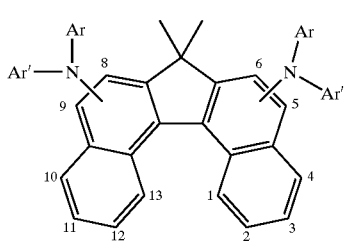
(II)

wherein Ar and Ar' are independently substituted or unsubstituted aromatic groups and said N atoms are bonded to two of carbon atoms 1–14 in structure (I) or carbon atoms 1–6 and 8–13 in structure (II), respectively, and wherein said carbon atoms 1–14 in structure (I) or 1–6 and 8–13 in structure (II) not bonded to said N atoms are unsubstituted or substituted with halogen atom, alkyl group, substituted alkyl group, alkoxy group, substituted alkoxy group, thioalkoxy group, substituted thioalkoxy group, cyano group, amino group, mono- or disubstituted amino group, hydroxyl group, mercapto group, aryloxy group, substituted aryloxy group, arylthio group, substituted arylthio group, carbocyclic aromatic group, substituted carbocyclic aromatic group, heterocyclic aromatic group, substituted heterocyclic aromatic group, heterocyclic group or a substituted heterocyclic group.

9. The compound of claim 8 having structure (I), substituted at carbon atoms 7 and 8 with identical aryl amine groups.

10. The compound of claim 8 having structure (II), substituted at carbon atoms 5 and 9 with identical aryl amine groups.

11. A light emissive compound having electron withdrawing groups bonded to a [5] helicene or dibenzofluorene core having the following structure (III) or (IV):

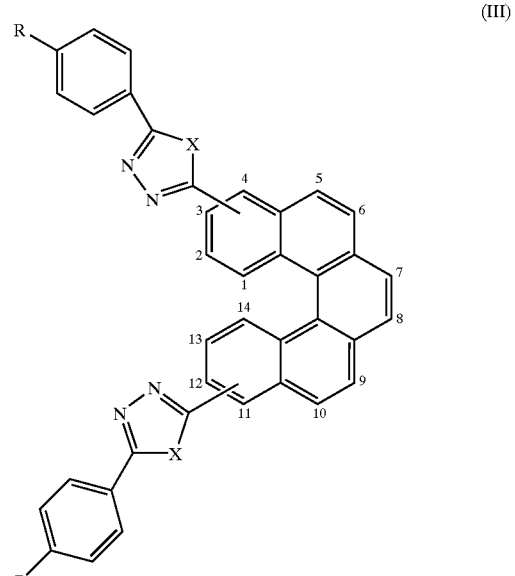
(III)

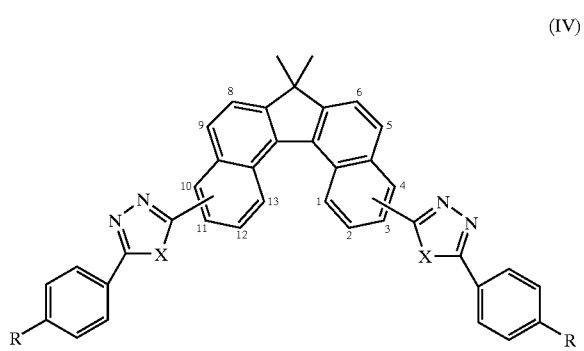
(IV)

wherein X is oxygen, sulfur or substituted or unsubstituted nitrogen, and R is H or hydrocarbon wherein said electron withdrawing groups are bonded to two of carbon atoms 1–14 in structure (I) or carbon atoms 1–6 or 8–13 in structure (II), respectively, and wherein said carbon atoms 1–14 in structure (I) or 1–6 or 8–13 in structure (II) not bonded to said N atoms are unsubstituted or substituted with halogen atom, alkyl group, substituted alkyl group, alkoxy group, substituted alkoxy group, thioalkoxy group, substituted thioalkoxy group, cyano group, amino group, mono- or disubstituted amino group, hydroxyl group, mercapto group, aryloxy group, substituted aryloxy group, arylthio group, substituted arylthio group, carbocyclic aromatic group, substituted carbocyclic aromatic group, heterocyclic aromatic group, substituted heterocyclic aromatic group, heterocyclic group or a substituted heterocyclic group.

12. The compound of claim 11 having structure (III), substituted at the 7 and 8 positions with identical electron withdrawing groups.

13. The compound of claim 11 having structure (IV), substituted at the 5 and 9 positions with identical electron withdrawing groups.

14. An electroluminescent device, comprising:

a transparent anode;

a cathode; and a layer of emissive [5] helicene material between the anode and the cathode having the following structure:

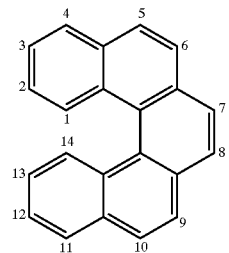

wherein the [5] helicene material is substituted with two identical arylamino groups of the formula Ar(Ar')N— wherein Ar and Ar' are the same or different, substituted or unsubstituted, aromatic groups, and said [5] helicene material has hole transport ability in said device, and wherein positions 1–14 not occupied by said arylamino groups are unsubstituted or independently substituted with halogen atom, alkyl group, substituted alkyl group, alkoxy group, substituted alkoxy group, thioalkoxy group, substituted thioalkoxy group, cyano group, amino group, mono- or disubstituted amino group, hydroxyl group, mercapto group, aryloxy group, substituted aryloxy group, arylthio group, substituted arylthio group, carbocyclic aromatic group, substituted carbocyclic aromatic group, heterocyclic aromatic group, substituted heterocyclic aromatic group, heterocyclic group or a substituted heterocyclic group.

* * * * *